(12) United States Patent
Andrews et al.

(10) Patent No.: US 10,088,422 B2
(45) Date of Patent: Oct. 2, 2018

(54) RAMAN SPECTROSCOPY FOR DETERMINATION OF COMPOSITION OF NATURAL GAS

(71) Applicant: SCHLUMBERGER TECHNOLOGY CORPORATION, Sugar Land, TX (US)

(72) Inventors: Albert Ballard Andrews, Wilton, CT (US); Andrew Speck, Milton, CT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 123 days.

(21) Appl. No.: 14/981,136

(22) Filed: Dec. 28, 2015

(65) Prior Publication Data

US 2017/0184502 A1   Jun. 29, 2017

(51) Int. Cl.
*G01N 21/65* (2006.01)
*G01N 33/28* (2006.01)
*G01J 3/44* (2006.01)

(52) U.S. Cl.
CPC ............... *G01N 21/65* (2013.01); *G01J 3/44* (2013.01); *G01N 33/2835* (2013.01)

(58) Field of Classification Search
CPC ........ G01N 21/65; G01N 33/2835; G01J 3/44
See application file for complete search history.

(56) References Cited

U.S. PATENT DOCUMENTS

| 4,577,110 | A | 3/1986 | MacBride et al. |
| 5,867,266 | A | 2/1999 | Craighead |
| 6,064,897 | A * | 5/2000 | Lindberg ........... A61B 5/14532 356/301 |
| 6,507,401 | B1 | 1/2003 | Turner et al. |
| 6,590,647 | B2 | 7/2003 | Stephenson |
| 6,678,050 | B2 | 1/2004 | Pope et al. |
| 6,841,779 | B1 * | 1/2005 | Roehner ............ G01N 33/2811 250/339.06 |
| 7,114,562 | B2 | 10/2006 | Fisseler et al. |
| 7,719,676 | B2 | 5/2010 | DiFoggio |

(Continued)

FOREIGN PATENT DOCUMENTS

| JP | 2009540582 A1 | 11/2009 |
| WO | 2011/147620 A1 | 12/2011 |

OTHER PUBLICATIONS

M.L. Shand and H.P. Jenssen, "Temperature Dependence of the Excited-State Absorption of Alexandrite," IEEE Journal of Quantum Electronics, 19(3), pp. 480-484, 1983.

(Continued)

*Primary Examiner* — Dominic J Bologna

(57) ABSTRACT

Apparatus and method for Raman-spectrography-based measurement of the composition of gas mixture in a high-temperature borehole. The method includes any of determining molar densities of individual alkanes of the mixture, introducing refractive index corrections, utilization of reference species internally to the measurement apparatus, correction for the effect of self-absorption and cross-absorption, as well as minimizing fluorescence when a liquid fraction is present in the borehole. The apparatus is configured to detect vibrational bands of CH, OH, CC, HS, NN and CO functional groups as well as collective modes in the fingerprint spectral region.

13 Claims, 15 Drawing Sheets

(56) References Cited

U.S. PATENT DOCUMENTS

| | | |
|---|---|---|
| 7,821,635 B2 | 10/2010 | Pope et al. |
| 8,269,961 B2 | 9/2012 | Mostowfi et al. |
| 8,786,840 B1 | 7/2014 | Woodruff et al. |
| 9,068,962 B2 | 6/2015 | Schneider et al. |
| 2002/0094007 A1 | 7/2002 | Peterson et al. |
| 2003/0048450 A1 | 3/2003 | Pope et al. |
| 2003/0169414 A1 | 9/2003 | Benz et al. |
| 2004/0073120 A1* | 4/2004 | Motz ............... A61B 5/0075 600/478 |
| 2005/0007583 A1 | 1/2005 | DiFoggio |
| 2005/0084912 A1 | 4/2005 | Poponin |
| 2006/0055919 A1* | 3/2006 | Lee ..................... G01J 3/44 356/301 |
| 2007/0076199 A1 | 4/2007 | Ode |
| 2007/0081157 A1 | 4/2007 | Csutak et al. |
| 2008/0111064 A1 | 5/2008 | Andrews et al. |
| 2008/0149819 A1 | 6/2008 | Zhdaneev |
| 2008/0247425 A1 | 10/2008 | Welford |
| 2010/0044103 A1 | 2/2010 | Moxley et al. |
| 2010/0195679 A1 | 8/2010 | Kroupa et al. |
| 2013/0104827 A1 | 5/2013 | Woerner et al. |
| 2013/0188169 A1 | 7/2013 | Harrison et al. |
| 2014/0209794 A1 | 7/2014 | Woodruff et al. |
| 2014/0271437 A1* | 9/2014 | Grabbe ............... C01B 33/029 423/350 |
| 2014/0339412 A1* | 11/2014 | Speck ................. H01S 3/0627 250/269.1 |
| 2014/0369889 A1 | 12/2014 | Mostowfi et al. |
| 2015/0021020 A1 | 1/2015 | Whittaker et al. |

OTHER PUBLICATIONS

T. Sun, et al., "Analysis of the double exponential behavior in alexandrite for optical temperature sensing applications," Review of Scientific Instruments, 68(9), pp. 3442-3446, 1997.

A. Rapaport, et al., "Temperature Dependence of the 1.06-micrometer Stimulated Emission Cross Section of Neodymium in YAG and in GSGG," Applied Optics, 41 (33), pp. 7052-7057, 2002.

T. Dascalu and N. Pavel, "High-Temperature Operation of a Diode-Pumped Passively Q-Switched Nd: YAG/Cr, YAG Laser," Laser Physics, 19 (11), pp. 2090-2095, 2009.

F. Trager, "Springer Handbook of Lasers and Optics," Springer, New York 2007, 23 pages.

W. Koechner, "Solid-State Laser Engineering," 6th ed. Springer, New York, 2006, pp. i-xvi.

Partial European Search Report issued in equivalent European Application No. 12857402.7 dated Oct. 2, 2015 (5 pages).

Extended European Search Report for corresponding European Application No. 12857402.7, dated Jan. 18, 2016, 11 pages.

International Search Report and Written Opinion issued in the related PCT Application PCT/US2012/068125, dated Mar. 29, 2013, 12 pages.

Office action issued in the related JP application 2014547298, dated Sep. 29, 2016 (8 pages).

Background Filtering in Fiber Optic Raman Sampling Probes, Technical Note #3, InPhotonics (2 pages).

\* cited by examiner

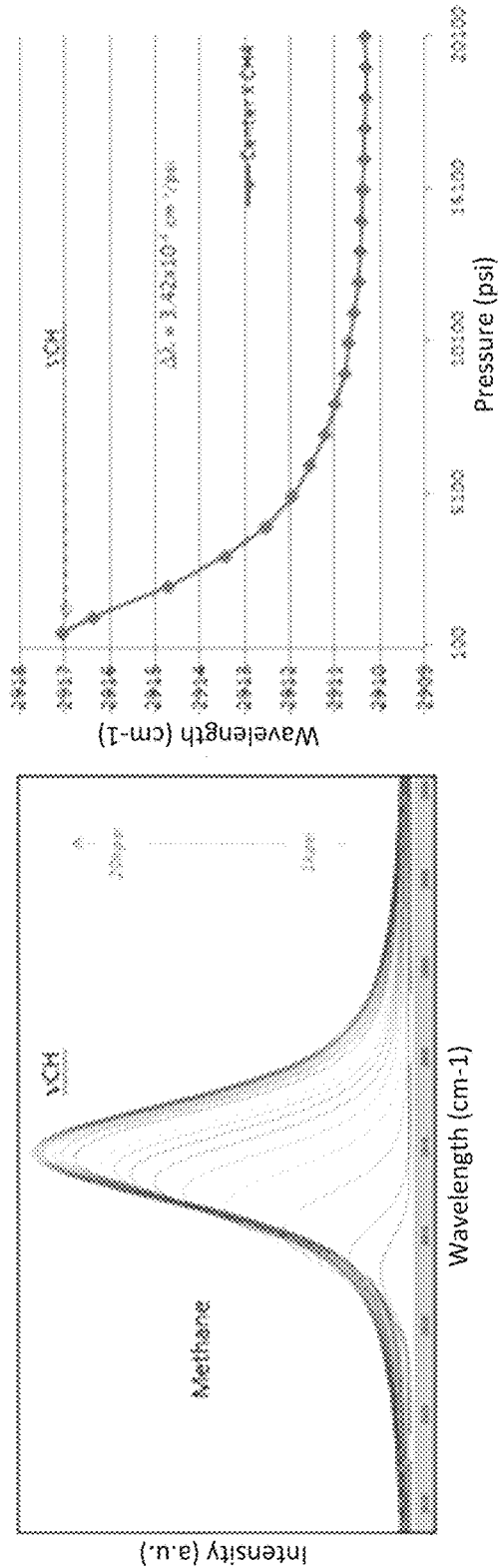

RAMAN SPECTROSCOPY FOR DETERMINATION OF COMPOSITION OF NATURAL GAS

TECHNICAL FIELD

The present invention relates to systems and methods for measuring the composition of natural gas in high-temperature environments and, in particular, to methodology for determination of such composition in a high-temperature borehole with the use of a Raman spectrograph.

BACKGROUND

Analysis of fluids (liquids and gases) in the petroleum industry provides identification of subterranean fluid characterization and variations in real time. Such analysis contributed to various useful finding, for example, to a determination that composition of hydrocarbons throughout the area of their distribution may be varied rather than homogeneous (caused by, for example, due to gravity, thermal gradients, biodegradation, water stripping, leaky seals, real time charging, multiple charging, and miscible sweep fluid injection, among other possible factors). The analysis is currently performed in a high-temperature environment in a so-called bore hole with the use of open-hole and cased-hole sampling tools that form a seal around a section of the borehole wall, or around casing perforations, while fluids in the formation are brought into the interior of the measurement tool.

Measurements effectuated with the use of Raman spectrometry (in which case a downhole measurement tool includes some type of a Raman spectrometer apparatus) rely on the strength irradiance of the Raman peak signal, often measured with the optical detector of the apparatus in a so-called back-scattering geometry, which is advantageous for production logging. Such peak strength or irradiance of the Raman-scattering optical signal, however, is subject to multiple variations during the measurement itself, caused not only by inhomogeneity of the target fluid chemical species and commingled flow of such species in the production well but also the power fluctuations of the laser light source used in the apparatus.

Such inhomogeneity of distribution of target chemicals and shortcomings of the measurements tool(s) begs a question of defining a reliable way to differentiate among the causes of variations in sought-after Raman measurement signal and appropriately correct or compensate for such variations to improve the quality, accuracy, and precision of the gas composition in the high-temperature environment of the borehole. This need remains unmet to-date in related industry.

SUMMARY

Embodiments of the invention provide an optical measurement system that includes a housing that defines an optical aperture and a closed volume (the closed volume is fluidly sealed from a medium outside of the housing). Inside the closed volume, there is disposed a laser source configured to generate light, as well as a light-delivery system positioned to provide optical communication between both the laser source and the medium outside of the housing and such medium and an optical detector of the optical measurement system. Optionally, the light-delivery system includes a reference optic judiciously chosen to generate radiation that represents Raman-scattering of light from the laser source and that has a Raman-scattering spectrum in which a spectral position of a spectral peak does not vary as a function of pressure. In some examples, the reference optic has a Raman-scattering spectrum in which a spectral position of a spectral peak also does not vary as a function of temperature.

Some embodiments of the invention also provide a method for determining composition of a mixture of alkanes. The method includes a step of acquiring, with an optical system that is disposed inside a fluidly-sealed closed volume and that includes a light source, first radiation to generate first data representing a first spectrum of the first radiation. Such first radiation represents Raman-scattering of light from the light source by the mixture of alkanes and/or other gases (e.g., $CO_2$, $N_2$, $H_2S$, etc.) that is located outside the closed volume and that is subject to high pressure and temperature. The first spectrum is formed at least in part by overlap between (i) a single CH stretch mode of a first alkane of said mixture, the first alkane having a chain of a first length; and (ii) collective modes or CC stretch modes of at least a second alkane of said mixture in a fingerprint region, the second alkane having a chain of a second length that is larger than the first length. The method further includes a step of removing the contribution of CH stretch modes of longer chain alkanes (in this example, the second alkane) to the combined integrated intensity of CH stretch modes of the first spectrum to determine the single CH stretch Raman band of the first alkane based on data representing intensity ratios of different modes of the collective modes. In some examples, the first alkane is methane.

Some embodiments provide a method for determining gas composition of a mixture of natural gases. The method includes a step of determining dependencies of intensities of radiations, respectively representing Raman-scattering of light from a light source by identified natural gases, as functions of respectively-corresponding molar densities of the natural gases. The method further includes a step of receiving first radiation representing Raman-scattering of light from the light source of the optical measurement system by the mixture to generate first data representing a first spectrum of the mixture. Light from the light source is delivered to the mixture through an optical window fluidly separating said optical measurement system from said mixture.

Additionally or alternatively, the method includes a step of receiving second radiation representing Raman-scattering of the light by a reference optical component of the optical measurement system to generate second data representing a second spectrum of the second radiation. A spectral position of a peak of the second spectrum does not vary as a function of any of pressure and temperature.

Alternatively or in addition, the method include correcting the determined dependencies of intensities by including respectively-corresponding linear terms that represent variations of corresponding indices of refraction of the natural gases with gas densities, which linear terms depends on respectively-corresponding molar refractivities.

Alternatively or in addition, the method includes correcting the first data to at least in part compensate for effects of cross-absorption and self-absorption in the mixture by configuring the optical measurement system such that response of the optical detector, of the measurement system, to any of the first and second radiations remains monotonic as a function of molar density of a corresponding gas.

A method further includes a step of determining gas composition of the mixture from the first data based at least in part on the dependencies of intensities.

Further features and aspects of example embodiments of the present invention are described in more detail below with reference to the appended Figures.

BRIEF DESCRIPTION OF THE DRAWINGS

Example embodiments of the invention will be more fully understood by referring to the following Detailed Description in conjunction with the not-to scale Drawings, of which:

FIGS. 5A, 5B are plots showing the spectral shift of the peak centroid of the $C_1$ (methane) Raman band with pressure ranging from 100 psi to 20,000 psi;

Figure 1:
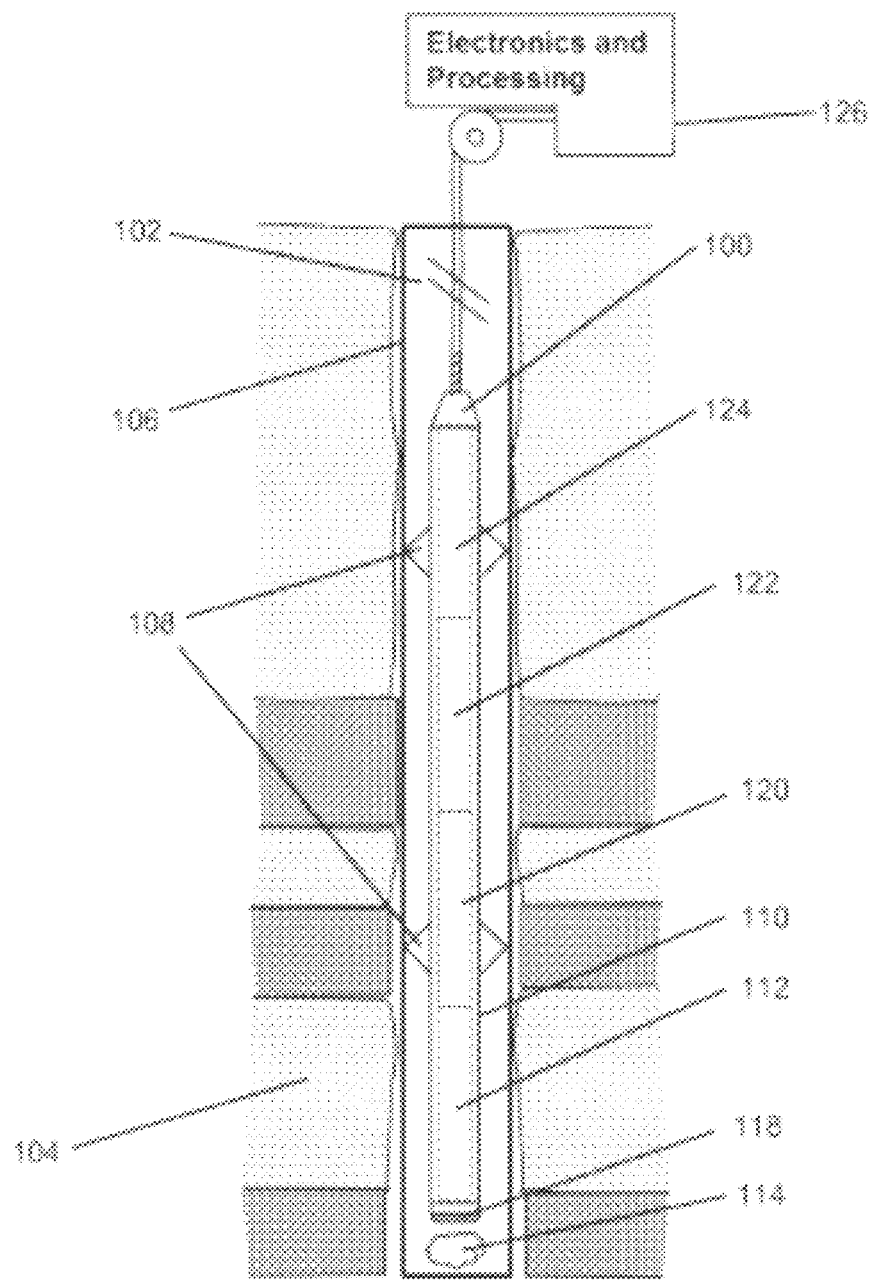
FIG. 1 is a schematic diagram of an embodiment of a downhole logging (measurement) tool.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

Different Raman-scattering signals produced by different stretch modes of different alkanes present in a mixture in the borehole and simultaneously acquired with an optical detector tend to mask each other in that the overall, integrated-among-the-different-Raman-peaks signal does not necessarily provide for clear identification of a chosen signal (in one example—a signal corresponding to CH stretch mode of methane). Some example embodiments address such problem of signal aggregation and overlap by removing the contribution of the CH stretch modes of the longer chain alkanes to the CH stretch region based, in part, on predetermination of intensities of Raman peaks corresponding to contributions of individual alkanes outside of the borehole.

Variations in the Raman scattering signal produced by a target chemical species and measured with a Raman-spectrometer-based tool can originate from different causes. (The terms "target chemical species," "target species," "chemical species of interest," "target chemical constituent" and the like may be used in this disclosure interchangeably.) One type of variation in the Raman scattering signal (referred to herein as the first type) stems from power variations of the optical output of the system used to generate the Raman scattering signal (for example, pulse-to-pulse power variations of light output from the laser source). Another type of variation in the Raman scattering signal (referred to herein as a second type), for example, is caused by the change(s) of the molar density of the target chemical constituent itself. According some example embodiments, the unsolved problems of distinguishing between different causes (first and second types) of variation of a useful, target Raman scattering signal produced by a target chemical species present in a high-temperature borehole and of compensating for the first type of variation as opposed to the second type of variation is addressed by (a) introducing into the optical path of the laser system output an additional, non-target (reference) chemical species the Raman-scattering signal response of which is a function only of the incident laser power; and (b) utilizing the data representing such Raman-scattering signal response from reference chemical species to compensate for variations in the Raman scattering signal received from the target species. The non-target species (or non-target chemical composition) may be configured, for example, as an optical component made of material that includes such non-target species and that is installed in the pulsed laser system across an optical path along which the target Raman-scattering signal is acquired with the logging tool including the pulsed laser system.

Alternatively or in addition to the solution of the above-stated problems, the problem of deviation of the target Raman scattering signal from being linearly-dependent on the molar density of the target species may be solved at least in part by (i) judiciously defining the focal length of the light-collecting optics of the present apparatus to ensure that a first derivative of the function representing the dependence of the acquired Raman scattering signal on the molar density remains positive within the range of measurement while the output of the optical detector formed in response to light acquired from the target species remains monotonic as a function of the molar density of the target species; and (ii) recovering the true concentration of the measured target species by normalizing the measured Raman scattering signal by an appropriately chosen exponential absorption factor.

In addition, the problem presented by the unwanted optical background caused by fluorescence process(es) in a liquid fraction of the target species, triggered with light used to excite the Raman scattering radiation, is solved at least in part by utilizing the light source configured to generate Raman-scattering-exciting light at a wavelength at which the contribution of fluorescent processes to the light-output produced by the target species is negligible as compared to that of the Raman-scattering processes.

In accordance with some embodiments, disclosed are methods and apparatus configured to determine a composition of natural gas in a high-temperature borehole with the use of a Raman spectrograph. Some embodiments provide a method for determining the molar densities of methane and other natural gas components (such as ethane, propane, butane, pentane carbon dioxide, nitrogen, and hydrogen sulfide, to name just a few). Some embodiments further provide a method for applying index refraction corrections; a method for correction of the measurement errors caused by effects of self-absorption and cross-absorption; and a method for avoiding or at least minimizing fluorescence when a liquid fraction, undesirably contributing to the measurement, is encountered during the measurement. Some embodiments further include a logging apparatus utilizing an internal crystal configured as a reference standard. An example of the proposed Raman spectrograph apparatus (interchangeably referred to herein as Raman spectrometer) is configured to detect the vibrational bands of functional groups such as CH, OH, CC, HS, NN, and CO, for example, as well as collective modes in the fingerprint region (which term is used to denote a pattern of molecular vibrations specific to identified analytes, and corresponds to the frequency region from 400 $cm^{-1}$ to 1800 $cm^{-1}$). While specific values chosen for this embodiment are recited, it is to be understood that, within the scope of the invention, the values of all of parameters may vary over wide ranges to suit different applications.

Examples of a solid-state laser-based Raman spectroscopy tool, used for determination of a Raman peak in the borehole, are described in U.S. Pat. No. 7,821,635, U.S. Patent Application Publication No. 2008/0111064, and U.S. Patent Application Publication No. 2014/0339412, each of which is hereby incorporated by reference in its entirety and may be referred to throughout this disclosure. Methodology for calculating compositional production rates in commingled gas wells, characterized by commingled flows of chemical species in the borehole and requiring knowledge of the flow rates for corresponding contributing zones, is detailed in U.S. Patent Application Publication No. 2015/0021020, which is incorporated by reference herein in its entirety.

Section 1: Example of a Production Tool Equipped with a Raman Spectrometer Apparatus.

An example embodiment of the production (downhole) tool 100, used in a gas condensate well, is schematically diagrammed in FIG. 1 and detailed in U.S. Patent Application Publication No. 2014/0339412. The pressures, temperatures, and fluid densities encountered in gas condensate wells produce a multi-phase flow with a phase separation as the gas and liquid flow to the surface.

The production logging tool 100 is disposed within a borehole 102 that traverses an earth formation 104. The borehole 102 includes a casing 106 and the tool 100 is typically lowered, during operation, into the casing 106 via a wireline cable and centered within the casing with the help of a set of centralizers 108. During production logging, formation fluid (such as formation liquid and/or formation gas) is extracted from different pay zones of the earth formation 104. As the formation fluid flows to the surface, the production logging tool 100 is used to monitor the characteristics (for example, the composition) of the fluid. The tool 100 includes a housing 110 that lodges a plurality of modules. At one end, the housing 110 includes an optical module 112 configured to perform spectroscopic measurements on a sample of the formation fluid 114 (for example, Raman spectroscopy measurement, and/or laser-induced breakdown spectroscopy measurement). The optical module 112 includes appropriate optics, at least one optical detector, and a light source such as a laser. In operation of the tool 100, the laser light is scattered back from the fluid sample (with which the optical module 112 is in optical communication through the window 118), collected by the optics, and acquired by the detector. In this case, the window 118 may be located at the lower end of the tool 100, while in related embodiment (such as that described, for example, in reference to FIG. 2 of U.S. Patent Application Publication No. 2014/0339412) the window may be located on a sidewall of the housing 110.

Additional modules cooperated with the optical module 112 may include, for example, a power module 120 (configured to generate ad provide power to the laser and the detector of the optical module) and an amplification module 122 (including electronic circuitry configured to amplify an electrical signal produced as an output by the optical module and representing backscattered light acquired by the detector). The production logging tool may further include a telemetry system 124, structured to provide communication between the production logging tool and electronic circuits and processing system 126 (which may include a programmable computer processor in operable communication with tangible, non-transitory storage medium contacting program code that at least partially governs the operation of the logging tool). The system 125 may be located outside of the borehole. In one example, the telemetry system 124 communicates the electrical signal from the optical module 112 to the surface.

It is noted that, the optical module 112 of the tool of the invention includes an appropriate IR-bandpass filter(s) (further discussed below) in lieu of a diffraction grating (which is typically used in conventional Raman spectrographs) to detect the gas species of interest. A specific band-pass filter—as compared to the diffraction grating that arguably may provide higher-spectral resolution—is intentionally chosen to increase the reliability of the tool operating at high-temperature and under high-pressure of the borehole and to allow for use of large area detectors (which would be simply impractical when the diffraction grating is used), thereby allowing to substantially reduce the overall cost of an embodiment of the tool as compared to that of the tools of related art. Related embodiments of the optical module and of the overall tool of the invention are detailed in US 2014/0339412 and are within the scope of the invention. Although a specific tool 100 is provided in this example, it should be understood that example embodiments may be provided in connection with any suitable tool, including tools that have features differing from those of tool 100.

Section 2: The Use of Spectral Peak(s) of Gas(es) for Measurement Calibration.

Specific to the high-temperature borehole conditions, for example, methane ($C_1$) has a single CH stretch Raman band (around 2912 $cm^{-1}$); longer chain alkanes have CH stretch bands that overlap with the methane band and each other; for example, ethane ($C_2$) has two CH stretch bands (2888 $cm^{-1}$, 2944 $cm^{-1}$), propane ($C_3$) has six CH stretch bands (2874 $cm^{-1}$, 2903-2965 $cm^{-1}$). See FIG. 2A, which illustrates plots representing, in arbitrary units, Raman CH stretch modes of $C_1$ (curve 200), $C_2$ (curve 201) and $C_3$ (curve 202) at 10 k psi for pure chemical components. Curves 203 and 204 show, for comparison, the transmission specta of dielectric filters used in the embodiment of the optical module 112, at 25 degrees C. and 200 degrees C., respectively.

Figure 2A:
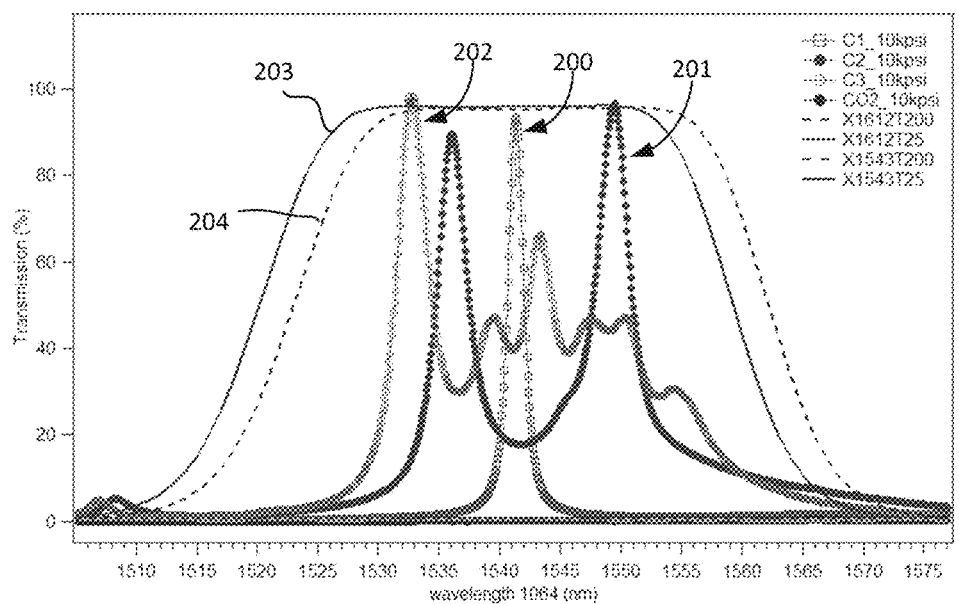
FIG. 2A illustrates Raman spectra of various CH stretch modes.
Figure 2B:
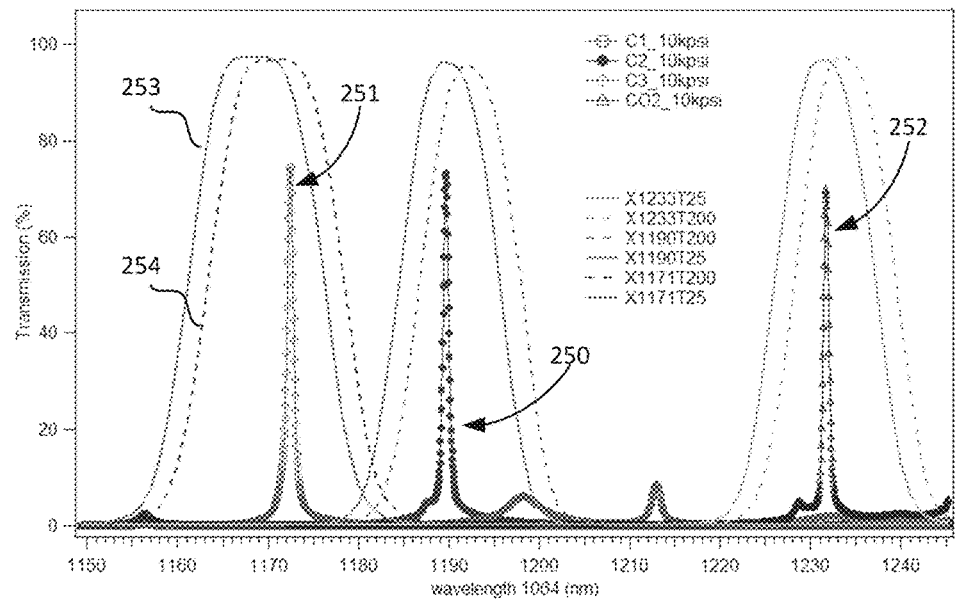
FIG. 2B illustrates Raman spectra of various CC and CO stretch modes.

Alkanes with two or more carbon atoms also have unique CC vibrational stretch modes in the "fingerprint region" as shown in FIG. 2B: ethane at about 993 $cm^{-1}$, and propane at about 869 $cm^{-1}$. $CO_2$ has two bands at 1386 and 1281 $cm^{-1}$. FIG. 2B shows plots representing the arbitrary-units spectra of the Raman CC stretch mode of $C_2$ (curve 250), $C_3$ (curve 251) and the CO stretch mode of CO2 (curve 252) at 10$k$ psi, for pure chemical components. Curves 253 and 254 show, for comparison, the transmission spectra of dielectric filter(s) used in some example embodiments of the invention, at 25 C and 200 C, respectively. The molar densities of longer chain alkanes, $CO_2$, $N_2$ and $H^2S$ can be determined by measuring the intensity of the CC, CO, NN and HS stretch modes. The used notations generally correspond to those accepted in related art: $C_1$ denotes methane only; $C_2$ denotes ethane only; $C_3$ denotes propane only; $C_4$ denotes n-butane and isobutane. Different isomers are conventionally denoted as $C_5$ (pentane, isopentane, and neopentane), $C_6$ (hexane, 2-methylpentane, 3-methylpentane, 2,2-dimethylbutane, and 2,3-dimethylbutane), and so on.

The optical data collected with the measurement system of some example embodiments (such as the tool 100 and, in particular, with the optical measurement module 112 implementations of which are addressed below) may contain measurement errors caused by effective acquisition-related integration of optical signals representing all the modes in the CH stretch region shown in FIG. 2A (for example mode $C_1$ shown as curve 200, mode $C_2$ shown as curve 201, and mode $C_3$ shown as curve 202). Accordingly, to determine a molar density of a given gas in the gas mixture (for example, a molar density of methane), the contribution of the longer chain alkanes to the CH stretch region is removed. Similarly, and with respect to the spectrum of FIG. 2B, a narrow band dielectric filter could cause an integration error in optical data representing the CC bands for $C_2$ (curve 250), and $C_3$ (curve 251), and $CO_2$ (curve 252).

To determine the methane molar density in a natural gas mixture, the contribution of CH stretch modes of the longer chain alkanes to the CH stretch region is to be accounted for. In some examples, the concentration of methane is determined by a subtraction procedure: the ratio of the CC stretch mode to the CH stretch mode for each longer chain alkane is determined. Such ratios (or ratio if singular longer chain alkane) are used to calculate a weighted contribution of the CH stretch modes of the longer chain alkanes to the CH stretch region. In this regard, the molar density of $C_1$ is then determined by subtracting the contribution of the CH stretch modes of $C_2$, $C_3$, $C_{4+}$ alkanes to the overall measurement of the CH stretch mode. This example methodology is further described below in Sec. 6.

Section 3: Examples of Optical Measurement System Configured to Address Environment-Caused Changes of Spectral Peaks.

An optical module of the logging tool (such as the tool 100) is designed, according to some example embodiments, to address several problems that have been left unsolved by the system of related art: the problem of temperature- and/or pressure-related variability of the spectral positions of the Raman peak(s) (which term refers to the peak(s) of Raman spectra) representing target chemical species measured in the borehole, and the problem of variability of the spectral intensities of such peaks as a function of variation of the optical output power of the laser source used as a source of light for performing the measurements. A skilled artisan familiar with related art knows that each of these can prevent the downhole logging systems from accurate determination of the target-species-related characteristics and, effectively, forces the related-art tools into producing measurement results with errors that an operator of the system is incapable of assessing (due to the unknown magnitude of the error) and correcting.

Figure 3A:
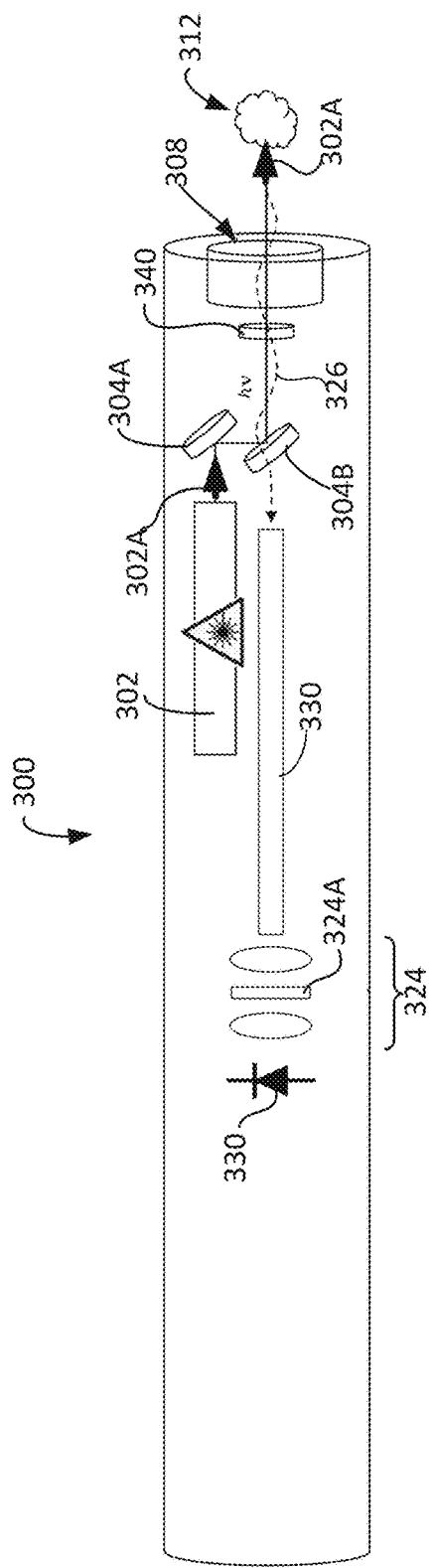
FIG. 3A is a diagram of an optical module for use with the downhole logging too of FIG. 1.

According to some example embodiments, an internal reference optical element disposed co-linearly with the excitation/light-collection optical elements is used to provide compensation of the above-mentioned errors. FIG. 3A illustrates some of the system components of the optical module 300, which include a laser source 302 configured to generate the radiant power in a form of the laser beam 302A and a light-beam-folding optics (shown as a combination of beamsplitters 304A and 304B) disposed to redirect the laser-output 302A through the optical window or viewport 308 outside of the module 300 and towards the region of interest (ROI) where the target chemical species 312 can be found during the operation of the tool. The material of the window 308 possesses such transmittance (both at the laser wavelength(s) and at the wavelengths of the "response" optical radiation 316, generated by the target species 312 in response to being irradiated with the laser output 301A) that is sufficient for collection of response optical radiation, which is the Raman scattered light, in a backscattering regime, and delivery of collected backscattered radiation 316 either via an optical fiber 320 or free-space (not shown) and a judiciously-chosen optical filter unit 324 to the optical detector 330. In some examples, the window 308 may also function as a pressure seal of the module 300. The optical radiation produced by the species 312 contains Raman photons (marked in FIG. 3A as hv and shown in a dashed line 326). For simplicity of illustration the light-focusing/light-collection optics, used as part of the optical module, some non-limiting examples of which are described in detail in U.S. Patent Application Publication No. 2014/0339412, has been omitted from the drawing. It is noted that in some implementations, the window 308 can be configured as a lensing component possessing non-zero optical power and forming a portion of the light-collection optics of the module 300.

It has been empirically confirmed that, in a typical downhole logging tool, a solid-state laser source 302 (operating, in one implementation, in a pulsed-regime) may exhibit pulse-to-pulse variations of output optical power of up to 10%. In another implementation, when the laser source operates in a continuous wave (CW) regime, similar variations of optical power may be observed. To compensate for the variability of the target Raman signal 326, the systems of related art average the results of the measurement of the target Raman signal(s) 326 to establish a mean value used as a value characterizing the species 312 outside of the tool 100. Referring again to FIG. 3A, in some embodiments, in contradistinction with the conventionally-used solutions of the related art and to compensate for not only the laser-output variability but also for the changes in the Raman signal 326 caused by variations in operational temperature and/or pressure, an optical component 340 referred to as a reference (or reference species or reference optic) is installed in the optical path of light 302A between the laser source 302 and the target species 312.

The reference 340 is so chosen that, when irradiated with the laser light-output 302A, generates a Raman peak at a characteristic wavelength that does not change as a function of change in operational pressure to which the logging tool is exposed in the borehole. The reference 340 is intentionally chosen to create a spectral Raman-type reference for the optical detector 330 by acting in contradistinction with the typical behavior of the Raman optical signal 326, a peak of which experiences spectral shift(s) and/or changes in amplitude caused by i) changes in operational characteristics of the laser 302 and/or chemical composition of the species 312, to which the light 302A is delivered at a given moment, and/or ii) changes in temperature and/or pressure in the borehole. It is appreciated that in terms of Raman spectroscopy measurement, the reference optical component 340 is configured as "reference chemical species" which, when present in addition to actual, target species 312 outside of the module 300, provides reference optical data facilitating the normalization of the target Raman signal data-acquisition process. As shown in FIG. 3A, the reference species 340 is structured internally with respect to the module 300 as a sufficiently optically-transparent element through which the Raman-signal-triggering laser radiation 301A is partially transmitted to be delivered to the target species 312. In related embodiments, the reference species can be disposed to operate in reflection (with the use of some additional beam-splitting optics). An example of such an embodiment is described in further detail below in connection with FIG. 3B. In other related embodiments, the window 308 of the optical module 300 can be configured to include the reference species 340 (for example, the optical window 308 can be made of material of the component 340, and be optionally configured to possess non-zero optical power.

Figure 4A:
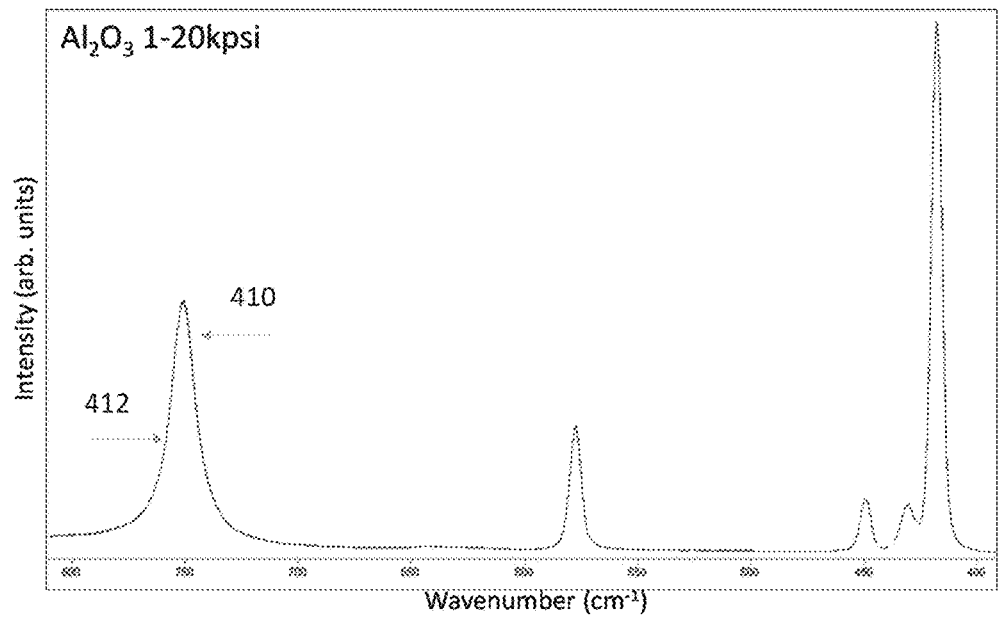
FIG. 4A includes two substantially overlapping plots, each representing Raman spectrum of radiation produced by sapphire at a corresponding level of pressure (impurity bands at 1 kpsi, 410, and 20 kpsi, 312)
Figure 4B:
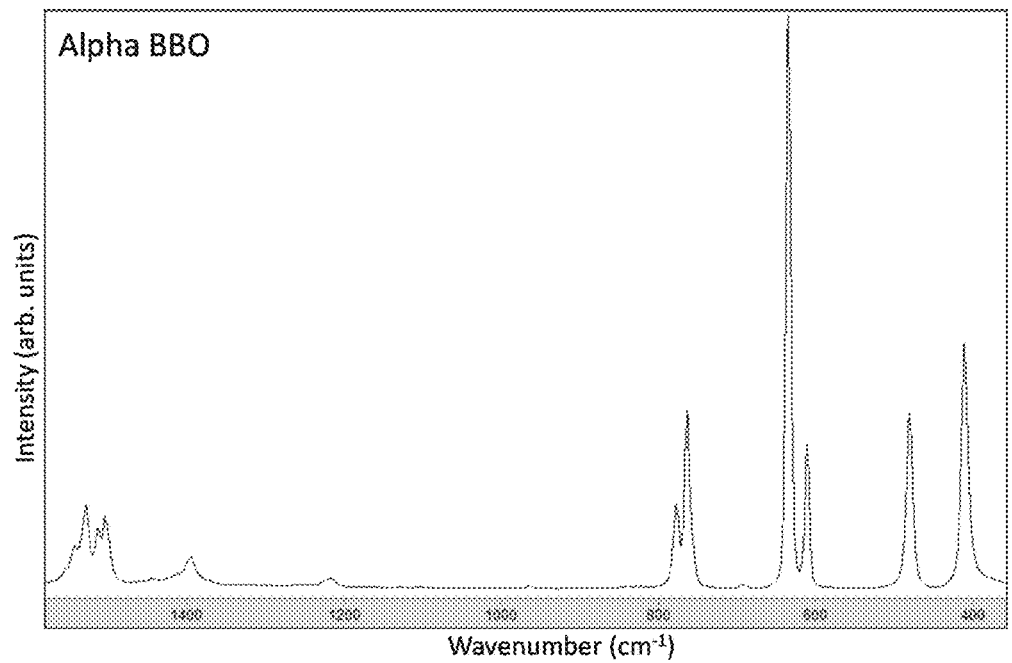
FIG. 4B is a plot representing Raman spectrum of alpha-BBO material.

The substance/material of the reference element 340 is judiciously chosen to generate a reference optical signal that does not optically interfere with the sought-after Raman signal(s) produced by the target gas (or gas-mixture) 312 and the spectral position of the peak of which does not change in responses to changes in the operational temperature and/or pressure during the measurement in the borehole. In other words, the reference signal produced by the reference species 340 falls outside the Raman spectral bands of the analyte gases of interest (a peak of the spectrum of the Raman scattering signal produced by the gas mixture does not overlap with a peak of the spectrum of the Raman scattering signal produced by the reference element 340). The Raman signal from the reference element 340 is used for calibration of the optical module. Sapphire is but one example of the material suitable for the reference 340; as shown in FIG. 4A, it has impurity bands below 800 cm$^{-1}$. Because of its ruggedness and mechanical strength, sapphire can also be used—in an embodiment in which the optical viewport 308 is configured, simultaneously, as a reference species element 340—as a pressure seal. An alpha-BBO crystal and calcite are examples of the material for use in construction of the reference element 340 to be disposed internally with respect to the optical module; see FIG. 4B.

When the reference 340 is used during the operation, the detector 330 receives simultaneously the Raman signal from the target mixture of gases from the borehole and the reference 340. With the use of "reference species" 340 in the optical path of the laser beam 302A, the normalized optical signal acquired by the detector 330, when the target 312 contains one and only, individual chemical species, is expressed as $$S_i = S_i^{meas}(S_{ref}^{ave}/S_{ref}) \tag{1}$$

where $S_{ref}^{ave}$ is the average value of the reference channel determined by calibration, while $S_i^{meas}$ and $S_{ref}$ are the values of the Raman signal acquired during the process of downhole measurement of the target gas-mixture 312 and during the process of the measurement of the reference species 340, respectively.

FIGS. 5A, 5B provide plots illustrating a 7 cm$^{-1}$ (or 8.25 nm) spectral shift of the peak centroid for the $C_1$ Raman band with pressure changing between 100 psi and 20,000 psi. To accommodate the spectral shift of Raman bands of the signal(s) from the target gas mixture with pressure, embodiments of the invention utilize filters 324A having spectral transmittance at corresponding central wavelengths that are judiciously chosen to ensure that the Raman spectral band stays within the filters' bandwidth(s) over the full range of pressures associated with the measurement, so that no signal from the target 312 is lost. Dielectric filters 324A for use in the optical module of the embodiment of the logging tool are configured as optical interference thin-film filters made of multilayer dielectric materials such as hard oxides. An example of a filter specification for the $C_1$ or methane channel includes a passband centered at 1543 nm+/−2 nm, 40 nm FWHM, blocking range of 1064 nm to 1700 nm (OD>5); the temperature shift of <2 nm within the range of temperature variation from about 25 C to about 200 C (or ~0.01 nm/C). Curves 203, 204 of FIG. 2A and 253, 254 of FIG. 2B provide representation of dependencies of spectral characteristics of typical filters used in the embodiment of the invention on temperature.

Figure 3B:
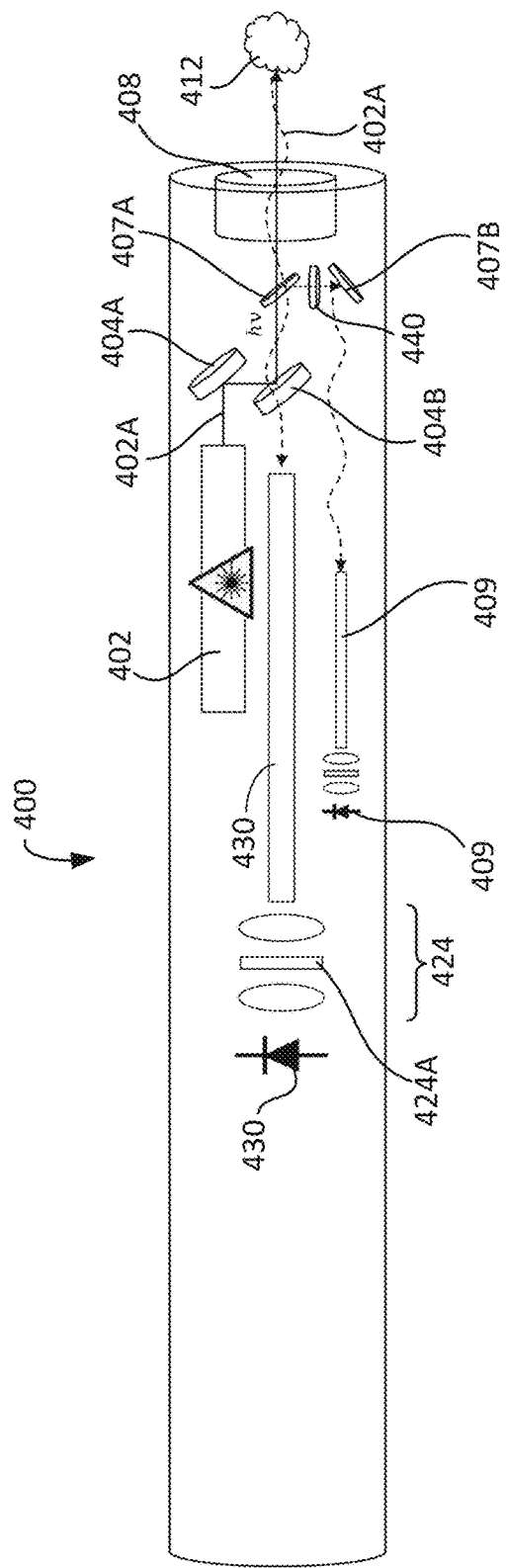
FIG. 3B is a diagram of an optical module for use with the downhole logging tool of FIG. 1.

FIG. 3B shows another example of an optical module. The optical module 400 of FIG. 3B includes many features in common with the module 300 described above. For example, the module 400 also includes a laser source 402 to generate laser beam 402A, light-beam-folding optics (illustrated as a combination of beamsplitters 404A and 404B) for directing a portion of the light from the laser source 402 to a species 412. The module 400 also includes an optical detector 330, a window 408. Each of the aforementioned components of module 400 has the same features of the corresponding components described above in connection with the module 300, except to the extent indicated otherwise.

As with module 300, the module 400 also includes a reference optical component 440 chosen that, when irradiated with the laser light-output 402A, generates a Raman peak at a characteristic wavelength that does not change as a function of change in operational pressure to which the logging tool is exposed in the borehole and has the same characteristics described above in connection with reference optical component 340 of module 300. However, in contrast to the reference 340 of module 300, the reference 440 is not in-line with the path of the Raman optical signal 426 as it travels from the species 412 to the optical detector 430.

Instead, the module 400 includes a second set of light-beam-folding optics including beamsplitters 407A and 407B. In this regard, the beamsplitter 407A splits a proportion of the laser light traveling from the beamsplitter 404B toward the species 412. This split portion of the laser light is directed by the beamsplitter 407A to the reference 440. In response, the reference 440 produces Raman scattered radiation that is directed by beamsplitter 407B to a second optical detector 409 to measure the Raman scattered radiation for the same purposes as set forth above in connection with module 300.

Section 4: Suppression of Background Caused by Fluorescence of a Liquid Fraction in a Borehole Mix of Materials.

Figure 6A:
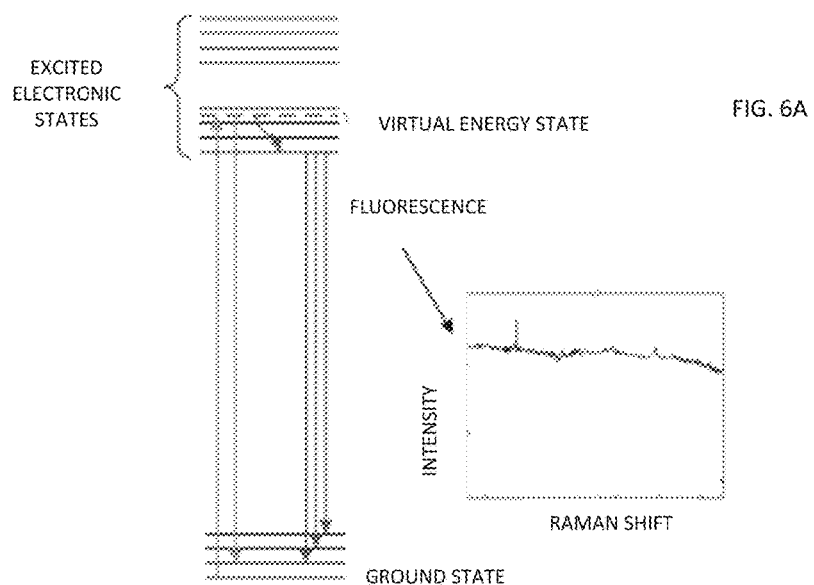
FIGS. 6A, 6B show energy level diagram to illustrate the relationship between the excitation energy and the molecular vibrational energy levels involved in Raman scattering and fluorescence processes. Switching to a longer excitation wavelength (FIG. 6B) moves the Raman emission to a spectral region where the fluorescence is minimized or non-existent.
Figure 6B:
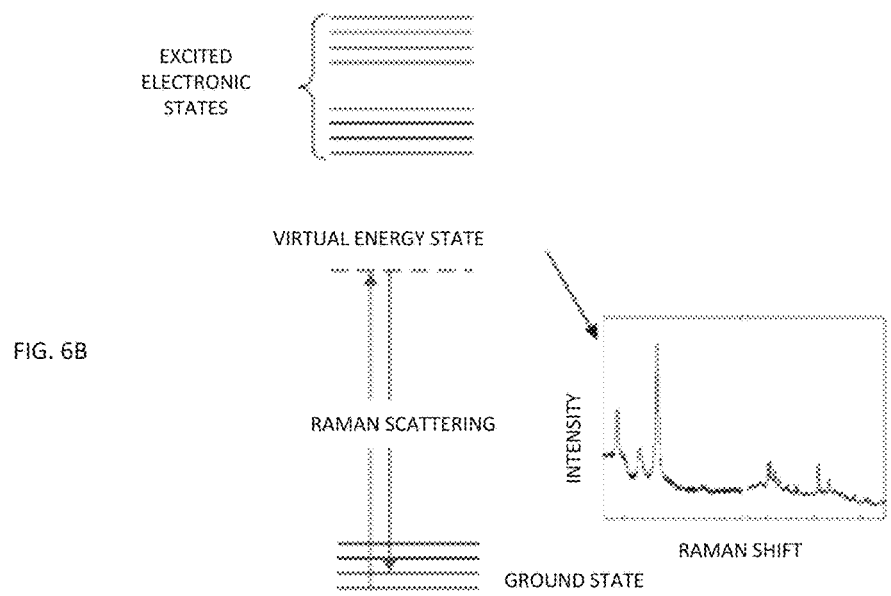

A fluorescence process is many orders of magnitude more efficient than the Raman scattering process; only a few ppm of a (fluorescent) impurity in a sample can partially or even completely obscure the Raman signal. Since a borehole-gas analyzer device is likely to encounter a liquid fraction during a logging run, either in the form of oil droplets or slugs, for example, the optical viewport 118 could be fouled by an oily film. If a liquid fraction is encountered, fluorescence background will add to the background in the gas fraction channels The energy level diagrams of FIGS. 6A, 6B illustrate the relationship between the energy of the excitation light and the molecular energy levels involved in Raman scattering and fluorescence processes. If the energy of light incident onto the target material is larger than the width of the gap between the highest occupied molecular orbital (HOMO, or ground state) and the lowest unoccupied molecular orbital (LUMO, or first excited state), the molecule can decay back to the ground state by emitting a (fluorescence) photon having lower energy than the photon of incident light (FIG. 6A).

Figures 7A, 7B:
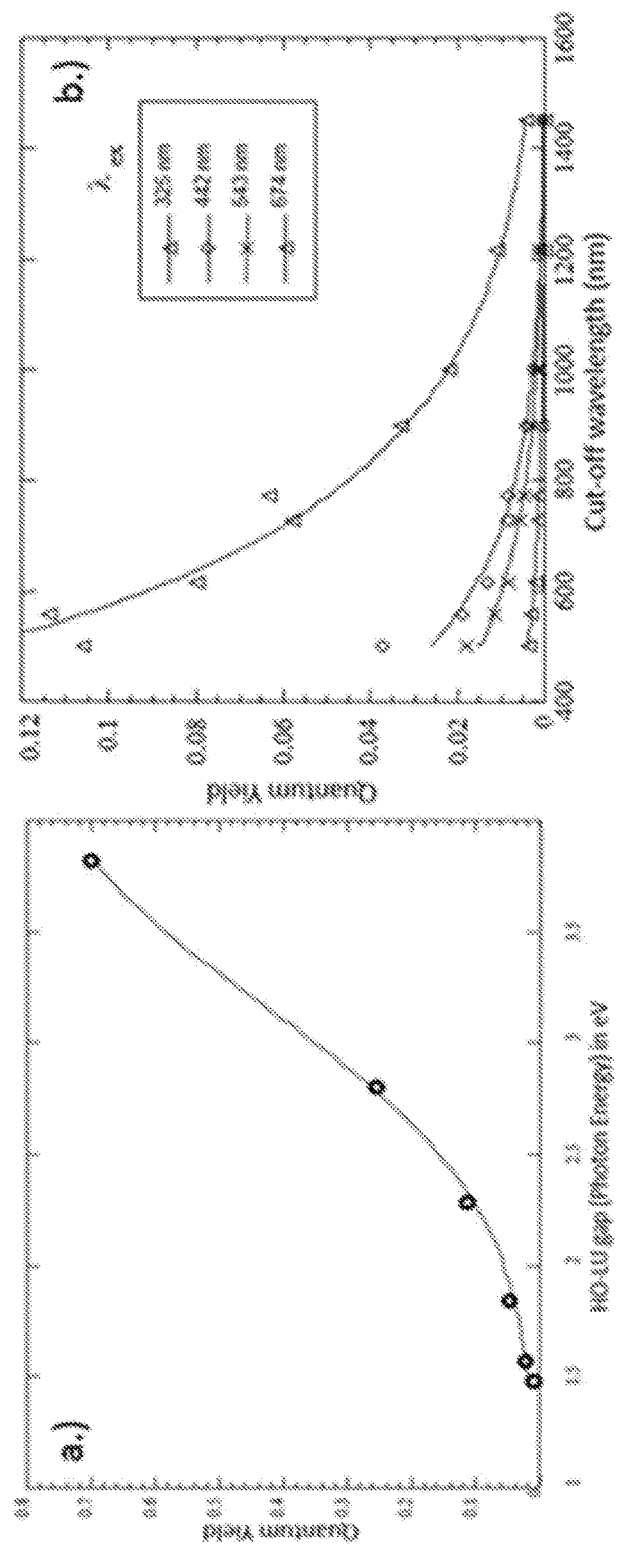
FIG. 7A presents a plot illustrating relationship between HOMO-LUMO gap and quantum yield for a Vixburg crude oil.
FIG. 7B presents plots illustrating relationship between quantum yield and cut-off wavelength (OD=1) for a series of crude oils (light to heavy)

The quantum yield (QY), defined as the ratio of emitted photons to absorbed photons, is indicative of fluorescence from the material in a borehole: higher quantum yields represent more fluorescence. For crude oil, for example, the QY is larger for smaller chromophores which are present in higher concentrations, and decreases for larger chromophores. FIG. 7A illustrates this as a function of the HOMO-LUMO. Conversely, the QY decreases as the position of the absorption edge increases (FIG. 7B). For example, when the excitation wavelength is chosen to be 532 nm (corresponding to energy of about 2.33 eV), the quantum yield is approximately 0.5. With a 1064 nm laser excitation (or 1.17 eV in photon energy), the QY is reduced by about an order of magnitude.

Some embodiments are based on a realization that the increase in net signal-to-noise ratio gained by suppressing fluorescence due to shift of the excitation wavelength towards longer wavelengths is sufficient, nevertheless, to compensate for the accompanying reduction of the Raman signal (caused by corresponding reduction of the Raman cross section). According to some embodiments, therefore, fluorescence of a gas mixture in a borehole is minimized by using laser light at a longer excitation wavelength (for example, a NIR wavelength, in one embodiment: 1064 nm). The energy of such laser light is insufficient to excite the molecule across the HOMO-LUMO gap, which minimizes fluorescence from the liquid fraction that may be present. At the same time, sufficient energy remains to excite the molecule into a virtual state inside the band gap (as shown in FIG. 7B), that is the Raman state.

Figure 8:
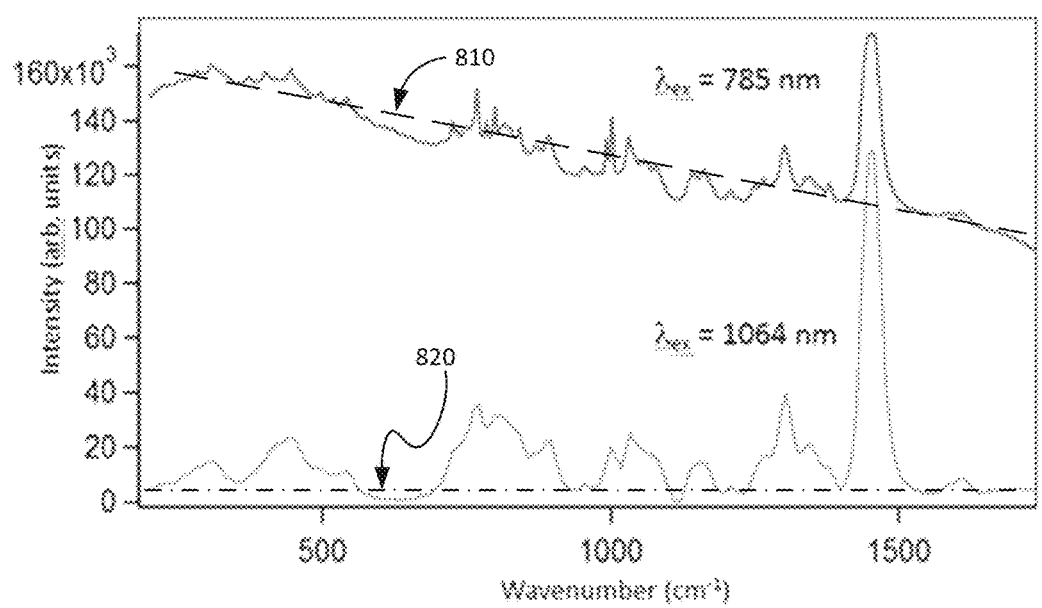
FIG. 8 shows plots representing Raman spectra (in the fingerprint region) of the liquid fraction of a gas condensate, independently excited with light at two different wavelengths. For a 785 nm excitation light, a significant optical background, caused by trace amounts of fluorescent chromophores, is observed as evidenced by a non-zero-slope of curve 810; for a 1064 nm excitation light, no fluorescence is excited and the corresponding background curve 820 has a substantially zero slope.

FIG. 8 illustrates this point for the liquid fraction of a gas condensate for two cases: a laser-caused excitation at 785 nm and that at 1064 nm. At 785 nm excitation, the fluorescent background is visibly present (as shown by a non-zero slope of the baseline/background-line 810), while for a 1064 nm excitation, no fluorescence background is present (as evidenced by a zero slope of the baseline/background-line 820).

In related embodiments, advantage is taken of deep ultraviolet resonance (DUV) Raman spectroscopy. (The DUV excitation light can be generated, for example, with quadrupling the frequency of a solid state infrared laser using non-linear optics principles. For example, a quadrupled 998.4 nm source will produce 248.6 nm photons. The 248.6 nm light excites Raman scattered photons below the onset of absorption in one ring aromatics (for example, benzene and toluene and xylene). The region 250-270 nm is a fluorescence free region. The Raman cross section is also enhanced by a factor of ~256 relative to the initial wavelength of 998.4 nm because the Rayleigh scattering efficiency is proportional to $1/\lambda^4$.

In related implementations, the use is made of a pulse-gated scheme to compensate for the presence of background fluorescence signal. The Raman scattering takes place on a faster time scale than fluorescence relaxation, >10 ns. Accordingly the data acquisition is gated so that Raman photons are collected even before the fluorescent signal is generated—specifically, only within the first 0.1 ns-to-1 ns of each excitation pulse, in response to a trigger signal sent to the amplifier of the electronic circuitry with which the optical detector is equipped, which trigger signal instructs the circuitry to store or collect only counts during this initial time interval.

In yet other related embodiments, a multi-wavelength modulation scheme may be employed. The fluorescence background is substantially spectrally flat ("featureless") and remains essentially unchanged when the energy of exciting light is modulated. By shifting the Raman excitation wavelength to different—but closely spaced—frequencies the Raman peaks may be separated from the background using processing algorithms.

Section 5: Correction of Errors Caused by Cross-Absorption and Self-Absorption Processes.

Figure 9:
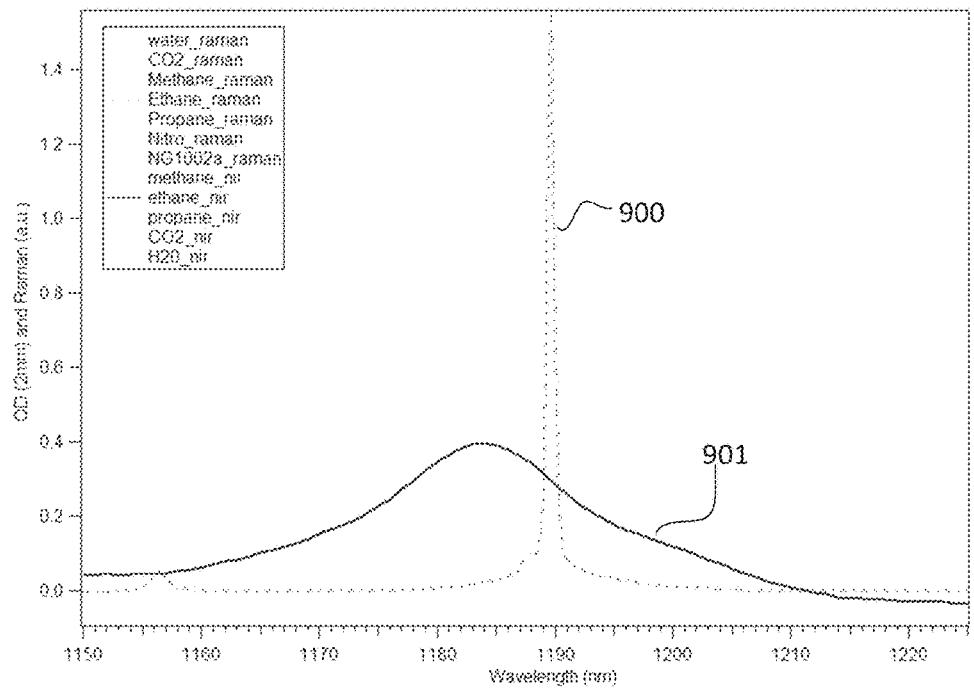
FIG. 9 illustrates the spectral overlap between the NIR absorpbtion band of ethane, 901, with the ethane Raman CC stretch mode, 900, caused by excitation of the borehole gas species with laser light at NIR wavelength.
Figure 10:
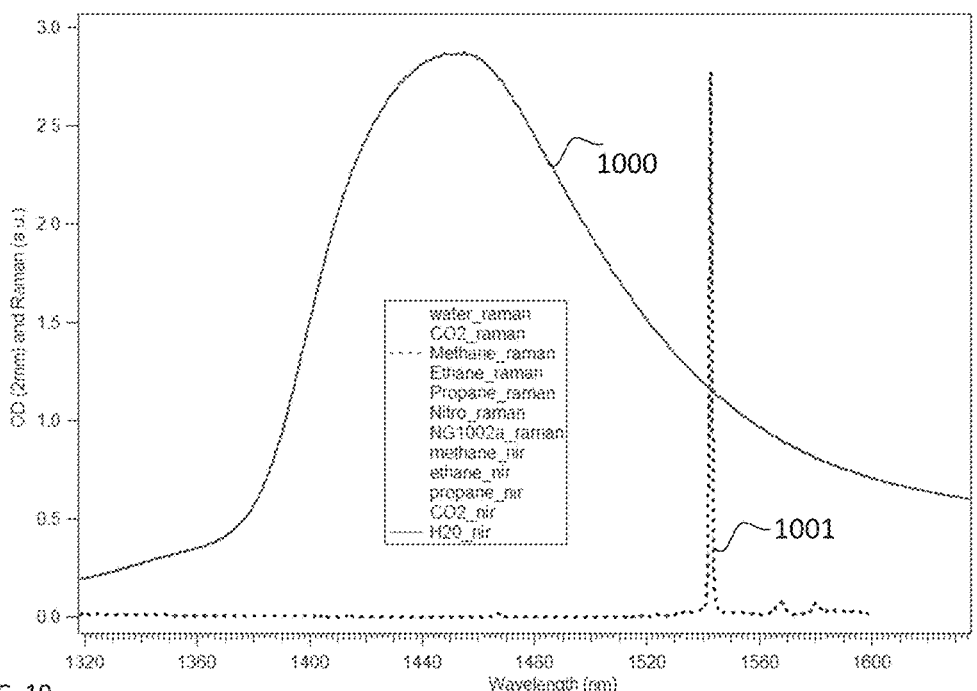
FIG. 10 illustrates the spectral overlap between the NIR absorpbtion band of water molecules, 1000, with the methane Raman CH stretch mode, 1001, caused by excitation of the borehole gas species with laser light at NIR wavelength.
Figure 11:
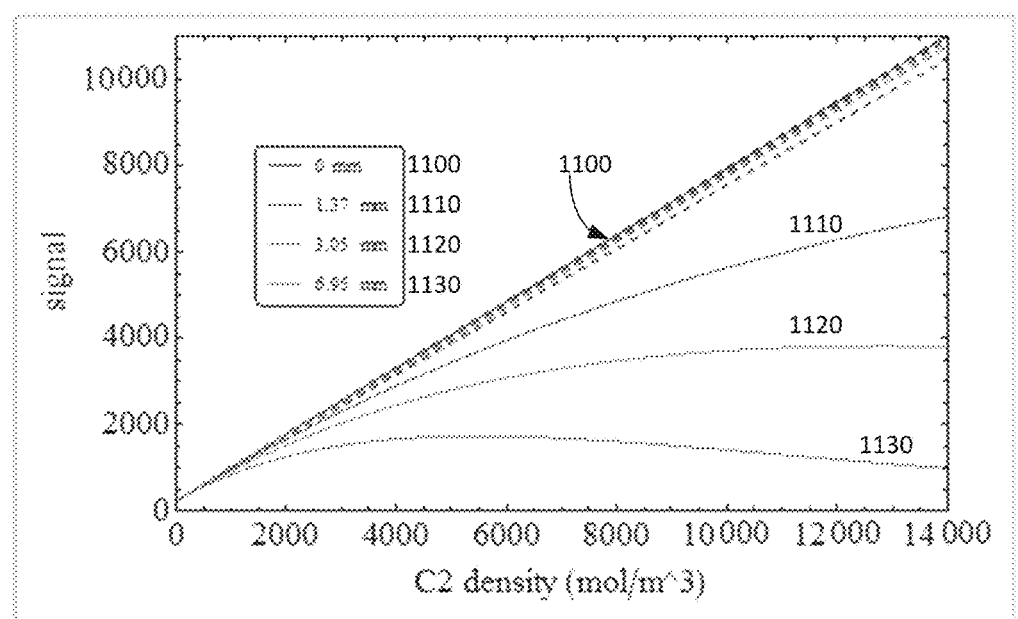
FIG. 11 shows plots illustrating the effect of self-absorption, occuring during the empirical determination of gas-composition with an embodiment of the tool of the invention, on the output data representing the molar density of ethane for various focal lengths (in mm) of the light-collecting optics of the optical module of the embodiment, and deviation of such data from the reference linear functional dependence.

Another practical problem addressed by some embodiments relates to the use of an MR laser for the excitation of the Raman signal, which is discussed in U.S. Patent Application Publication No. 2014/0339412. When the Raman excitation occurs at a NIR wavelength, one or more of the Raman spectral bands may end up overlapping with NIR absorption bands of the target gas molecules. In the case of such spectral overlap with the absorption spectrum of a specific analyte in the borehole, the absorption process is referred to as self-absorption, while in the case of overlap with any of absorption spectra of other molecules in the well-bore, such as water molecules, for example, the absorption process is referred to as cross-absorption. An example of the self-absorption process is shown in FIG. 9. Here, the MR absorption band of ethane 901 overlaps with the ethane Raman CC stretch mode 900. An example of cross-absorption is shown in FIG. 10, where the MR absorption band of water 1000 overlaps with the methane Raman CH stretch mode 1001. In reference to FIG. 11, both self-absorption and cross-absorption processes cause the measured Raman intensity to deviate from a linear dependency on the molar density discussed above.

To solve this problem, some example embodiments are configured to implement a twofold solution. On the one hand, the deviation of the measured (Raman signal vs molar density) function from the linear dependence is additionally adjusted to recover the true concentration of the measured species. This is achieved by normalizing the measured signal by an appropriately chosen exponential absorption factor. On the other hand, the focal length of the light-collection optics of the optical module 112, 300 (typically disposed between the beamsplitter 304B and the window 308) is judiciously structured to ensure that a first derivative of the function representing the dependence of the Raman signal intensity (acquired with the optical detector 330) on the molar density remains positive within the range of measurement while the output of the optical detector formed in response to light acquired from the target species remains monotonic as a function of the molar density of the target species. It was empirically found that to achieve such optical-detector response, the focal length of the light-collecting optics of the optical module 112, 300 should be chosen in the range of several tens of centimeters (for example, 20 to 30 cm, preferably less than 20 cm, more preferably less than 15 cm).

More specifically, the effect of self-absorption and cross-absorption is accounted for by adding an absorption term into the model for the signal generation by a gas molecule i, of molar concentration $n_i$ and a given optical path length x:

$$S_i(x) = \beta_i n_i \Pi_j 10^{-\alpha_j n_j x} \quad (2)$$

Here, the product is defined over all molecules, j, with each having an absorption coefficient of $\alpha_j$. The tool 100 measures the total signal acquired through the light-collecting optics at all path lengths between the target gas-mixture and the detector, which requires the electronic circuitry to integrate over all these possible pathlengths (with a coefficient, $\in(x)$, representing giving the light-collection efficiency at a given pathlength):

$$S_i = \int_0^{x_{max}} \in(x) S_i(x) dx \quad (3)$$

Figure 12A:
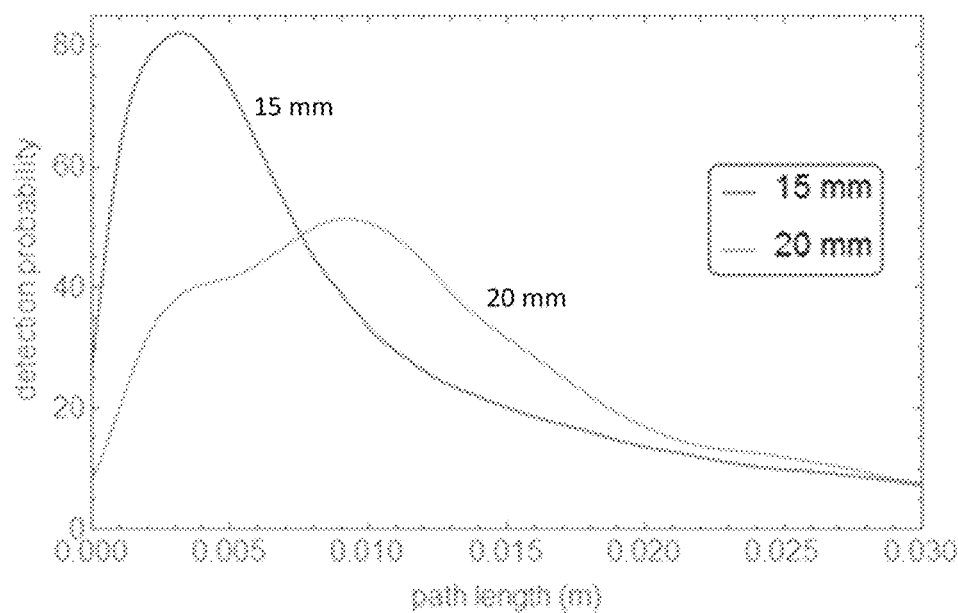
FIG. 12A illustrates efficiency of the Raman-scattering signal acquisition as a function of a borehole pathlength for two different focal lengths of the light-collecting lens system of the optical module of an embodiment of FIG. 1.

To determine the coefficients in these formulae, both an empirical calibration and a calibration based on ray-tracing was employed. The $\in(x)$ coefficient was calculated through ray-tracing the light-collecting optical component of the optical module 300. The light-collection efficiency is determined, in this case, by varying the source position in the well bore and calculating how many light rays are coupled from the collecting optics into the fiber bundle 220. FIG. 12A shows the result of this calculation for two different choices of collimation and fiber focusing lens; one has a focal length of 15 mm and one has a focal length of 20 mm.

The absorption coefficient, $\alpha_j$, can be and was measured by a UV-VIS-NIR transmission spectrometer for different target molecules of interest. As an example, water has an absorption coefficient of 0.005977 $m^2$/mol at 1630 nm (corresponding to the detection wavelength for Raman-scattered light from water).

The Raman scattering coefficient, $\beta_i$, can be obtained during calibration measurement runs, using pure samples of the molecules of interest and correcting for any potential self-absorption using the equations above.

Figure 12B:
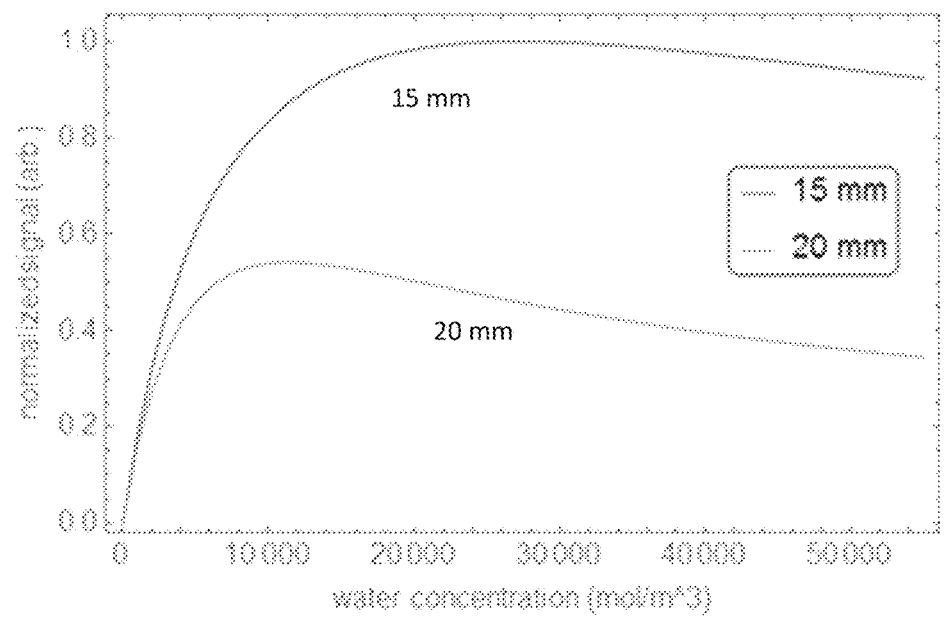
FIG. 12B shows a water Raman-scattering signal acquired with a light-collecting optics having two different focal lengths as a function of liquid fraction concentration.

To further minimize the errors causes by absorption in the measurement of the target Raman scattering radiation, the focal length of the light-collection collimating lens has to be judiciously chosen. This choice is done by utilizing the equation above and predicting the signal from molecules of interest at different densities (as shown in the example of FIG. 12B). In the specific example of FIG. 12B, 15 mm-focal-length collection optics has a broader range of concentrations within which a meaningful variation in the signal can be observed (prior to saturation and then decline). In contrast, the use of the 20 mm-focal-length collection optics demonstrates, in this specific example, lower levels of the overall signal and has a significant region where the signal is actually declining when the concentration is increased increasing concentration. The 15 mm version of the collection optics is, therefore, preferred in this example.

To compensate for still inadvertently-remaining nonlinearities shown in FIG. 12B even with the choice of a proper focal length of the light-collection optics, the previously-given tool model equations are utilized. These predict the measured signal for a given the concentration of all measured molecules. Then, a nonlinear fit/inversion method is used to minimize the difference between the predicted signals and the actually-measured ones.

Section 6: Methodology of Extracting Raman-Scattering Data Representing a Single Peak from Integrated Measurement Data.

In accordance with some examples, to address the problem of integration of optical data acquired from the mixture of alkanes, stated in Section 2, measurements of the gas-composition under high-pressure conditions typical for a borehole are configured to take advantage of using one of spectral peaks of light acquired with the optical detector 330 for data calibration. An independent, laboratory-based measurement of pure gases is performed first to create a reference file with reference tabulated data. Then, during or after the downhole logging run, the composition of natural gas mixtures in a borehole is determined with the use of an appropriate inversion algorithm based on recorded empirical deviations from the reference calibration data.

Figure 13:
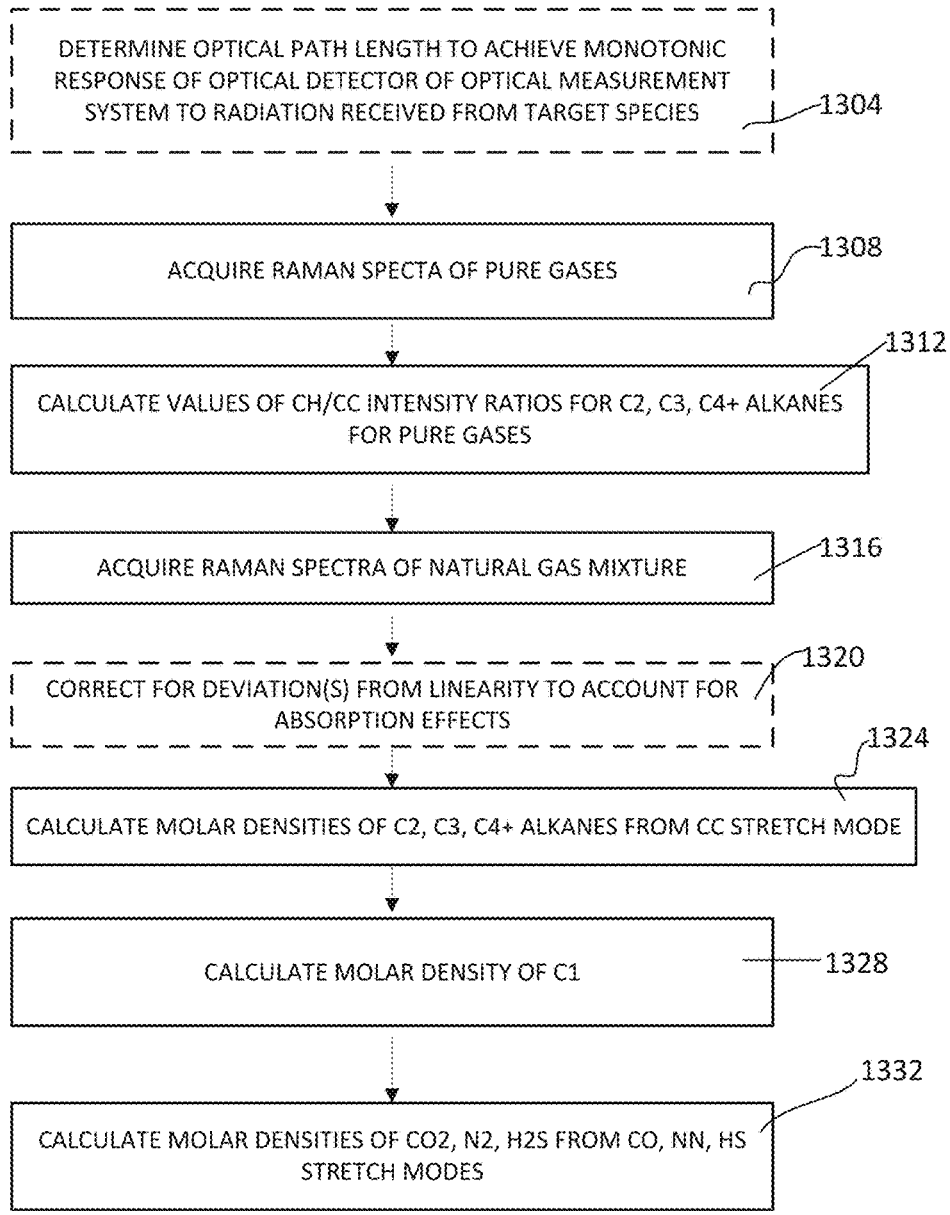
FIG. 13 is a flowchart illustrating steps of an embodiment of an algorithm for determination gas composition from molar densities of gas constituents.
Figure 14A:
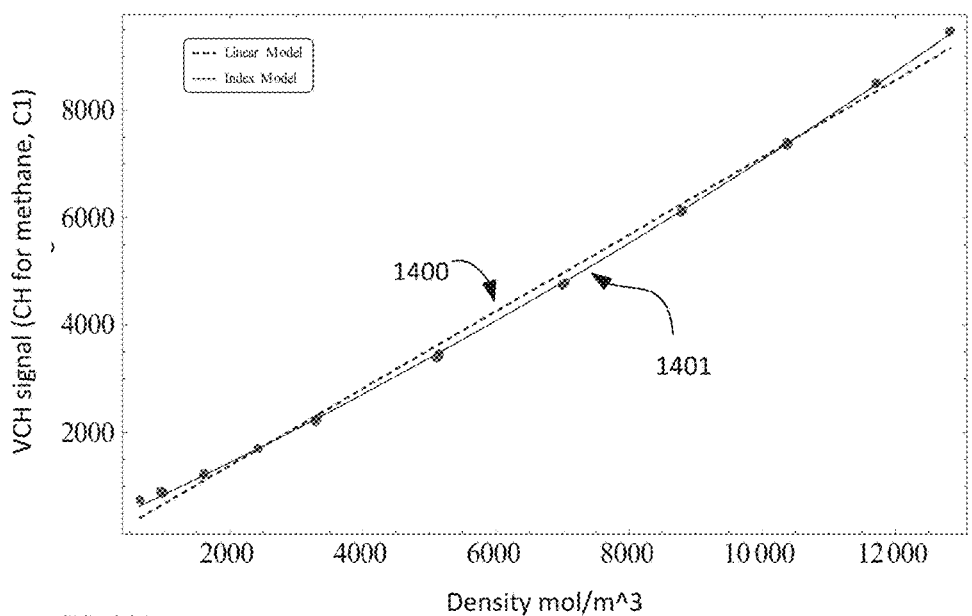
FIGS. 14A, 14B, 14C provide plots illustrating empirical 2d order correction introduced to correct for dependence of the sample volume on molar refractivity of gas and to determine the corrected dependence of Raman signal intensity on the molar density of gas.
Figure 14B:
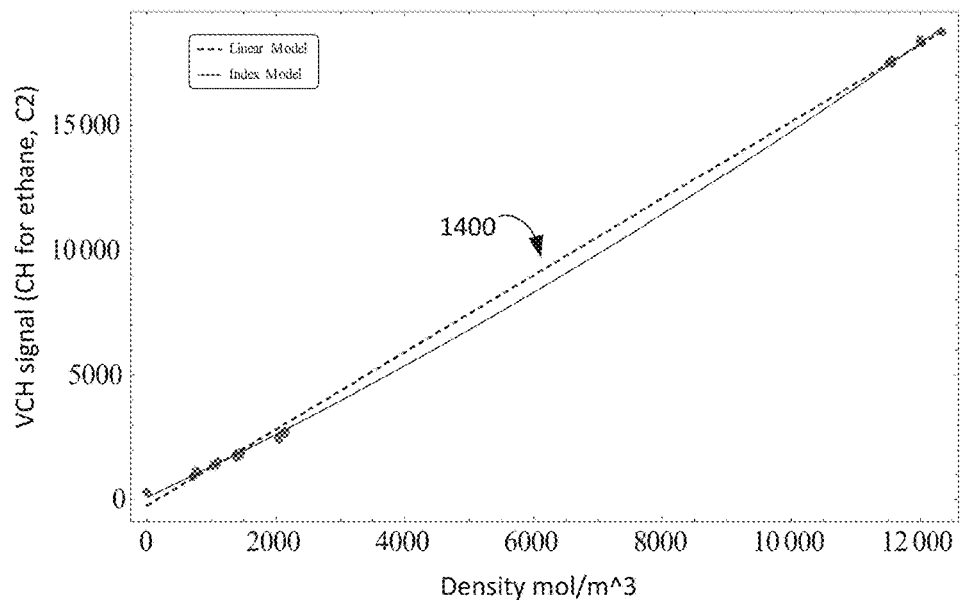
Figure 14C:
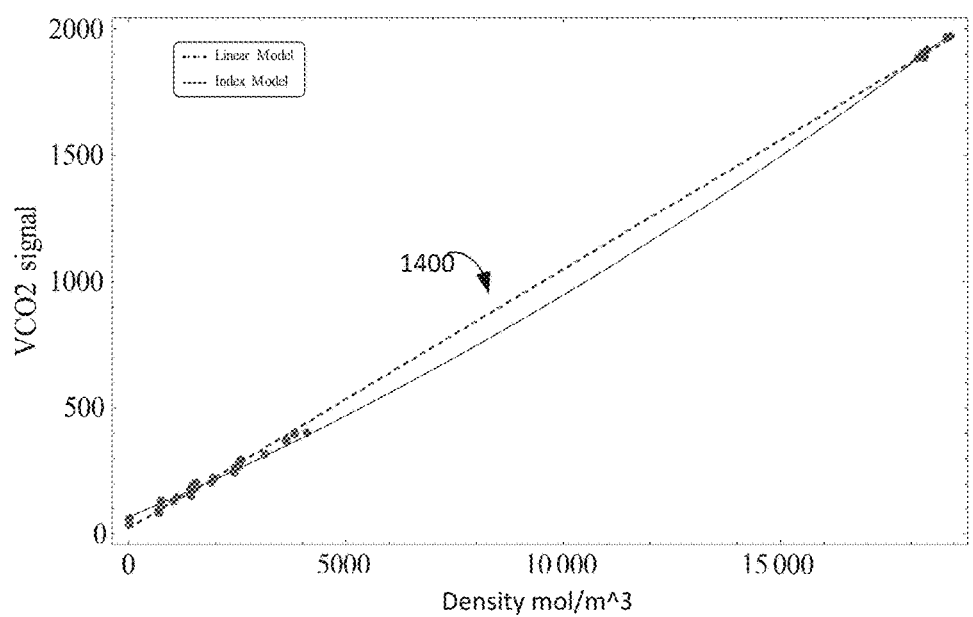

The flowchart of FIG. 13 illustrates an example of the measurement algorithm of the invention. Here, at step 1304, parameters of light-collecting optics of the optical module 112 are judiciously chosen to ensure that the optical response of the detector 330 remain monotonic as a function of the value of the molar density of the species being measured. At steps 1304, 1308, 1312 pure gases are measured in the laboratory environment to acquire and record calibration data that represent the intensity of a Raman signal as a function of molar density of a particular gas species. Such intensity, to the first order, is linearly proportional to the molar density (as shown by 1400 in FIGS. 14A, 14B, 14C, where curves in FIG. 14A represents CH for methane ($C_1$) and curves in FIG. 14B represents CH for ethane ($C_2$). Correction can be introduced by including additional linear response term(s) $1 + 3 r_m n_m$ to account for index variations with gas-density that affect the sample excitation volume, and to obtain a corrected dependence (shown in FIG. 14A as 1401A, for example) at step 1320. Here, the molar refractivity $r_m = (1/n_m)(n^2 - 1)/(n^2 + 2)$, $r_m$ is the number density, $n_m$ is the molar density of the gas, and n is the index of refraction of the gas. (Corrections accounting for self- and/or cross-absorption effects can be performed in addition.) During the actual logging run, such calibration data obtained at step 1312 are used in conjunction with the inversion algorithm to calculate the composition of natural gas mixtures in a borehole. Once the measurement of the natural gas mixture in the borehole is being performed, 1316, additional corrections accounting for self- and/or cross-absorption effects can be performed at step 1320.

As shown in FIG. 13, molar densities of various alkanes are determined from the empirically acquired CC stretch mode data, at 1324. The concentration of methane is determined by a subtraction procedure: the ratio of the CC/CH stretch mode for each longer chain alkane is used to calculate a weighted contribution to the CH stretch region. The molar density of $C_1$ is then determined by subtracting the contribution of the $C_2$, $C_3$, $C_{4+}$ alkanes to the CH stretch mode, at step 1328. The concentrations of longer chain alkanes, $CO_2$, $N_2$ and $H_2S$ are determined from the CC, CO, NN and HS stretch modes data, at step 1332. In the example when the ethane CC mode is analyzed, the calibration data acquired at step 1312 is used to calculate how much of the integrated area in the CH stretch channel is due to ethane. In this manner, the weighted contribution for each longer chain alkane ($C_2$, $C_3$, . . . ) is subtracted from the empirically acquired signals to form the remainders of data which, in turn, are used to calculate the methane concentration.

Inversion Algorithm. As mentioned above, an inversion algorithm is used for the determination of the composition of natural gas mixtures. The forward model defines the Raman-scattering response as a function of absolute densities of the measured analytes. By adjusting the inputs so that the predicted Raman-scattering response(s) match(e)s the measure response(s), the best-fit molar densities can be inferred with the optimization method of choice (such as, for example, nonlinear fitting, Bayesian inference, and the like).

As an example, a model is considered that includes Raman-scattering optical signals for l gases and o measurement channels, $X_i$, that are linearly proportional to the absolute densities of the analytes, $n_j$, through a response matrix, M (dimensioned as o rows by l columns):

$$X=Mn$$

where X and n are vectors.

In a real-world practical situation, the response function is likely not to be a simple linear matrix. For a Raman-scattering measurement, it was determined that there exists an additional linear response to the densities of the gas (due to index variation with density, which affects the sample volume) and an exponential dependence between measurement channels due to absorption such that the signal for a given channel can be expressed approximately as $$X_i = (M_{ij}n_j)(1+3n_k r_k)10^{-\alpha_{io}n_o d}$$

Here, $r_k$ is the molar refractivity of gas k, $\alpha_{io}$ is the absorption coefficient of gas o at measurement channel i, and d is the optical pathlength within the sample volume. While the best-fit molar densities can be inferred with various optimization methods, it may be preferred to use Bayesian inference as that allows to cleanly define, through prior knowledge, the region of allowed molar densities and thus ensure the inversion occurs in a unique region.

Some embodiments have been described as including a processor controlled by instructions or programs defining the functions performed by the embodiments and stored in a tangible, non-transitory memory storage and delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Some of the processes performed by example embodiments of the invention have been described with reference to flowcharts and/or block diagrams showing the steps that may be combined, separated into separate operation steps and/or performed in a different order.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

While the invention is described through the above-described exemplary embodiments, it will be understood by those of ordinary skill in the art that modifications to, and variations of, the illustrated embodiments may be made without departing from the inventive concepts disclosed herein. For example, the algorithm for determination of a single peak of CH stretch mode of $C_1$ from the acquisition of spectrally-convolved Raman signals representing multiple peaks of multiple stretch modes of multiple alkanes (optionally including the inversion method), as discussed in Section 6, can be complemented with any of other inventive features discussed in the application, such as a feature directed to suppress background caused by fluorescence of a liquid fraction (when present in a borehole mix of materials), a feature directed to correction of errors caused by processes of self-/cross-absorption, or a feature allowing to decouple the acquisition of Raman scattering signals from variations of power of the laser source of the invention with the use of a built-in-the-optical-module reference component, to name just a few. In other words, disclosed aspects of the invention, or portions of these aspects, may be combined in ways not listed above. Accordingly, the invention should not be viewed as being limited to the disclosed embodiment(s).

The invention claimed is:
1. A method comprising:
directing light from a light source simultaneously to (a) a reference optic and (b) a mixture of fluids, thereby inducing
a first Raman-scattered radiation corresponding to the reference optic, wherein a spectral position of a peak of the first Raman-scattered radiation does not vary as a function of pressure or temperature, and
a second Raman-scattered radiation corresponding to the mixture of fluids;
compensating for effects of cross-absorption and self-absorption in the mixture of fluids by configuring the response of an optical detector such that at least one of (a) the first Raman-scattered radiation and (b) the second Raman-scattered radiation remains monotonic as a function of molar density of a corresponding gas;
detecting the first Raman-scattered radiation and the second Raman-scattered radiation; and
using a computer processor to determine composition of the mixture of fluids based on the second Raman-scattered radiation, wherein the determination includes using the first Raman-scattered radiation to compensate for variations in intensity of the light from the light source.

2. The method according to claim 1, wherein a peak of the first spectrum does not overlap with a peak of the second spectrum.

3. The method according to claim 1, wherein the mixture of fluids is comprised of a mixture of natural gases.

4. The method according to claim 1, wherein the using a computer processor to determine composition of the mixture of fluids includes calculating molar densities of gas components of said mixture.

5. The method according to claim 1,
wherein the detecting the first Raman-scattered radiation and the second Raman-scattered radiation is performed in an environment and for which a spectral position of the second Raman-scattered radiation varies as a function of i) pressure and temperature of the environment, and ii) chemical composition of the mixture of fluids.

6. The method according to claim 1, further comprising transmitting the light through the reference optic to illuminate said mixture.

7. The method according to claim 1, further comprising splitting a beam of the light to form a first beam illuminating the reference optic and a second beam transmitted through an optical window to illuminate the mixture of fluids.

8. The method according to claim 1, further comprising:
prior to directing light from a light source simultaneously to (a) a reference optic and (b) a mixture of fluids, determining, using an optical module, dependencies of intensities of Raman-scattered radiations by predetermined individual natural gases in response to light from the light source, as functions of molar densities of the individual natural gases.

9. The method according to claim 1, wherein the compensating is achieved at least in part as a result of adjusting a focal length of radiation-collecting optics of the optical measurement system.

10. The method according to claim 1, further comprising compensating for effects of cross-absorption and self-absorption in said mixture by accounting for pre-measure absorption coefficients of gas constituents of said mixture.

11. The method according to claim 1, wherein said using the computer processor to determine composition of the mixture of fluids includes calculating molar densities of alkanes from a stretch mode representing a constituent gas of the mixture of fluids.

12. The method according to claim 1, further comprising transmitting the first and second Raman-scattered radiation through an optical fiber to optical sensors configured to detect the first and second Raman-scattered radiation transmitted through the optical fiber.

13. The method according to claim 1, wherein the detecting is performed in a housing of a downhole production logging tool configured to analyze a formation fluid.

* * * * *